United States Patent [19]

Lecuru et al.

[11] Patent Number: 4,640,133
[45] Date of Patent: Feb. 3, 1987

[54] ULTRASONIC TESTING DEVICE PROVIDED WITH A ROLLING MEANS

[75] Inventors: Daniel Lecuru, Puteaux; Jean-Pierre Choffy, Rueil-Malmaison, both of France

[73] Assignee: Aerospatiale Societe National Industrielle, Paris, France

[21] Appl. No.: 852,125

[22] Filed: Apr. 15, 1986

[30] Foreign Application Priority Data

Apr. 17, 1985 [FR] France ............... 85 05826

[51] Int. Cl.⁴ .................................. G01N 29/04
[52] U.S. Cl. .............................. 73/639; 73/644
[58] Field of Search ................ 73/639, 644, 583

[56] References Cited

U.S. PATENT DOCUMENTS

| | | | |
|---|---|---|---|
| 3,628,375 | 12/1971 | Pagano | 73/639 |
| 3,714,816 | 2/1973 | Miller | 73/639 |
| 3,771,354 | 11/1973 | Miller | 73/639 |
| 4,302,976 | 12/1981 | Bull | 73/639 |
| 4,472,974 | 9/1982 | Dickson et al. | 73/635 |
| 4,519,251 | 5/1985 | Dickson | 73/639 |

Primary Examiner—Anthony V. Ciarlante
Attorney, Agent, or Firm—Fisher, Christen & Sabol

[57] ABSTRACT

An ultrasonic testing device of the type comprising a fixed hub with at least one ultrasonic transducer as well as an annular rolling means mounted for rotation on said hub and surrounding said transducer, this latter being mounted on the hub through a support whose external face opposite said transducer defines with the inner face of said rolling means a rotational sliding slit, the coupling between said support and said rolling means being provided by an ultrasonic liquid present in said slit, wherein a spongy resilient element is provided imbibed with said coupling liquid, said element being housed in a recess in said hub and being applied resiliently against the inner face of said rolling means.

8 Claims, 3 Drawing Figures

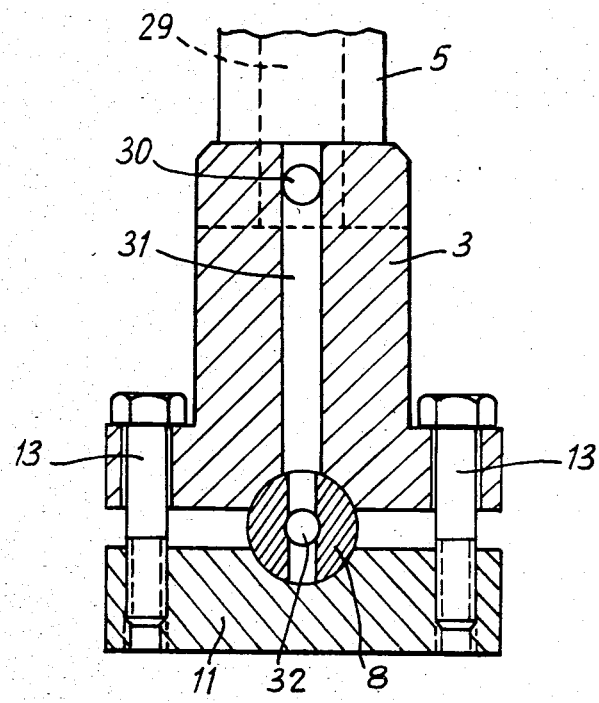
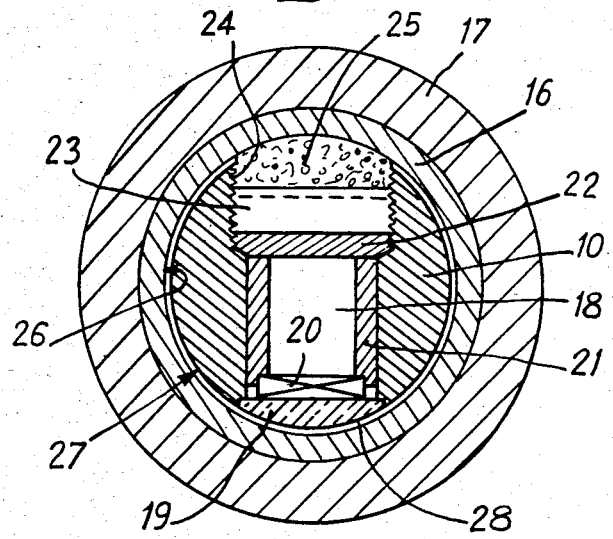

ULTRASONIC TESTING DEVICE PROVIDED WITH A ROLLING MEANS

BACKGROUND OF THE INVENTION

1. Field of the Invention

The present invention relates to an ultrasonic testing device having a rolling means. Although it may be used in numerous applications, it is more particularly described hereafter with respect to a particular application concerning the non destructive inspection of the bonded junctions of panels forming the skin of the fuselage of an aircraft.

It is known that the skin of the fuselage of an aircraft is formed from individual light alloy panels assembled together by bonded joints, themselves reinforced by rivetted junctions.

Such rivetted and bonded joints are subjected to great strain during the use of the aircraft, more particularly because of the compression and decompression cycles to which the fuselage is subjected. The result may be that zones of loosening develop from small bonding defects not detected during construction. Consequently, the junctions are weakened and it is therefore indispensible to periodically check the bonded junctions so as to know the state thereof.

The complete non destructive inspection of the bonded junctions of the skin of an aircraft could be carried out by means of an ultrasonic probe, emitting or receiving or combining the two functions. In a way known per se, there would be displayed on the screen, for assessing it, an abnormal ultrasonic echo variation caused by a bonding defect, detected in the zone explored, with respect to a normal known and standardized echo of the zone.

However, as is known, the quality of the measurable indications delivered by the usual ultrasonic probes depends on the ultrasonic coupling between the probe and the work piece to be studied. Now, such coupling is provided by a greasy substance (vaseline for example), which must be removed after the measurement by careful cleaning.

Consequently, what is p for a work piece of reasonable size, proves to be unusable when it is a question of aircraft fuselages, particularly large transport aircraft.

The result is then that it is practically impossible to test the junction of an aircraft fuselage using ultrasonic probes, requiring a coupling means between themselves and said fuselage.

2. Description of the Prior Art

Wheeled ultrasonic probes are already known for example from documents U.S. Pat. Nos. 3,628,375 and 4,302,976, intended for rolling over work pieces to be tested and requiring no greasy coupling therewith. Such probes comprise a fixed hub having at least one ultrasonic transducer, as well as an annular rolling means (wheel) mounted for rotation on said hub and surrounding said transducer.

In these known probes, the transducer is housed in a sealed chamber formed between the hub and said wheel and filled with an ultrasonic coupling liquid, internal to said probes. Thus, transmission of the ultrasounds between the transducer and the wheel is provided. However, there are numerous drawbacks:

because of the relative movement of the wheel with respect to the hub, the coupling liquid is "beaten", so that bubbles appear inside said liquid, these bubbles disturbing the measurements;

although seals are provided between the hub and the wheel, leaks of the coupling liquid occur, particularly through the ball or plain bearings by which the wheel is mounted on the hub;

such leaks themselves also cause the formation of bubbles and must then be compensated for; for that, a complementary liquid reservoir is provided, which increases the bulk of said probes.

It follows from the foregoing that such wheeled ultrasonic probes could not be used either for testing the junctions of the fuselage of an aircraft.

A wheeled ultrasonic testing probe is further known, more particularly from the document U.S. Pat. No. 4,472,974, in which the ultrasonic transducer is mounted on the hub through a support whose external face, opposite said transducer, defines with the inner face of said wheel, a rotational sliding slit; in this case, the volume of the coupling liquid contained between the hub and the wheel is smaller than in the probes of documents U.S. Pat. Nos. 3,628,375 and 4,302,976. However, such a construction does not overcome the drawbacks due to the formation of bubbles in the coupling liquid inside the probe and to leaks of this liquid outside the probe.

The purpose of the present invention is to overcome these drawbacks and to provide probes capable of being used more particularly for testing junctions of aircraft fuselages.

SUMMARY OF THE INVENTION

For this, in accordance with the invention, the ultrasonic testing device, of the type comprising a fixed hub with at least one ultrasonic transducer, as well as an annular rolling means mounted for rotation on said hub and surrounding said transducer, this latter being mounted on the hub by means of a support whose external face, opposite said transducer, defines with the internal face of said rolling means a rotational sliding slit, the coupling between said support and said rolling means being provided by an ultrasonic coupling liquid present in said slit, is remarkable in that it comprises a spongy resilient element imbibed with said coupling liquid, said element being housed in a recess in said hub and being applied resiliently against the inner face of said rolling means.

Thus, when said rolling means is applied to a work piece to be tested and is moved for rolling therealong, said spongy element deposits a film of coupling liquid on said inner face of said rolling member. This film then provides ultrasonic coupling of the transducer (through said support) with said rolling means. It will be noted that, with the invention, the amount of coupling liquid is extremely reduced and that there exists no liquid likely to be "beaten" by the relative movement of the rolling means with respect to the hub. Consequently, the formation of bubbles is inexistent. In addition, because of the instantaneous desorption and absorption power of the coupling liquid, the spongy element maintains the balance between the liquid which it contains and the liquid applied to the inner face of the rolling means. The desorbed liquid is therefore never in excess, so that the risks of leaks of liquid outwardly are also fairly small.

To further reduce the risk of liquid leaks towards the outside, there may be provided, on each side of said recess containing the spongy element and coaxially with said hub, disks of spongy material carried by said hub and applied by their periphery against the inner face of said rolling means. Preferably, each of these disks is pressed between a bearing face of said hub and the corresponding ball or plain bearing, serving for mounting the rolling means with respect to the hub.

Advantageously, a rigid wear and maintenance washer is provided between a spongy disk and the corresponding ball or plain bearing.

In an advantageous embodiment, instead of being bonded to its support, as is usual, the transducer is applied thereagainst by pressure means. Thus better centering of the ultrasonic beams and good ultrasonic coupling between the transducer and its support may be obtained. These pressure means may comprise a nut pressing said transducer through a resilient slug and a rigid centering guide.

Advantageously, said hub comprises a passage transversal to its axis and, inside said passage, are arranged said transducer support, said transducer, the means for placing the transducer on its support and said spongy element.

BRIEF DESCRIPTION OF THE DRAWINGS

The Figures of the accompanying drawings show how the invention may be constructed, by way of example.

FIG. 2 is a partial sectional view, along line II—II of FIG. 1, and

FIG. 3 is an enlarged sectional view through the wheel of the device, along line III—III of FIG. 1.

DESCRIPTION OF THE PREFERRED EMBODIMENT

Figure 1:
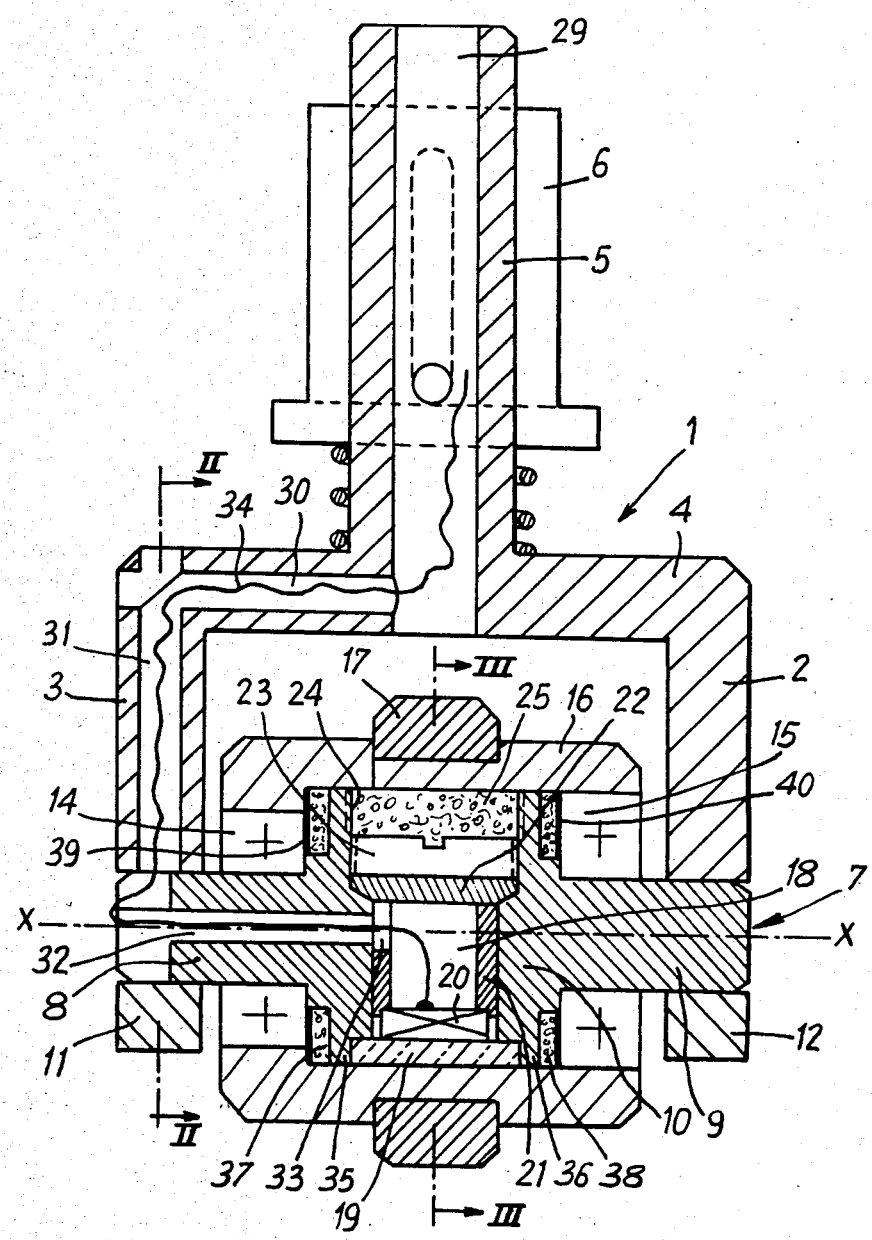
FIG. 1 is a sectional view of the device of the invention.

The embodiment of the device of the invention shown in the Figures, comprises a fixed assembly formed by a stirrup 1, in the shape of a U, having two parallel arms 2 and 3 connected together by a back 4. This back 4 is integral with a rod 5 having means 6 for fixing to a mobile member not shown.

Between the parallel arms 2 and 3 is held a fixed hub 7, with axis X—X, comprising two end shanks 8 and 9, connected together by a central cylindrical swollen portion 10. Hub 7 is secured to stirrup 1 by means of pressure plates 11 and 12 which, under the action of screws 13, lock said end shanks 8 and 9 against said arms 2 and 3 of stirrup 1.

On each side of the swollen central part 10 of hub 7 are disposed ball bearings 14 and 15, by means of which a cylindrical rim 16 may rotate about hub 7. A bearing ring 17 is firmly secured to rim 16.

The central swollen portion 10 of hub 7 is pierced with a pasage 18, transversely disposed with respect to axis X—X. The end of passage 18 turned outwardly of stirrup 1 is closed by a window 19, made for example from a material such as PLEXIGLAS (registered trademark), supporting a piezoelectric crystal 20 forming the ultrasonic transducer. This crystal is pressed against window 19 by means of a centering tube 21 fitting partially over the periphery of said crystal, without hindering the axial vibrations thereof. The centering tube 21 is urged towards crystal 20 by a resilient slug 22, itself pressed by a nut 23 screwed into a threaded portion of passage 18.

On the nut 23 side, opposite the piezoelectric crystal 20, passage 18 is formed with a recess 24, in which is disposed a spongy element 25 imbibed with the liquid providing ultrasonic coupling.

Between the inner face 26 of rim 16 and the outer face 27 of the cylindrical swollen central part 10, is formed an annular slit 28, visible in FIG. 3, in which its thickness has been exaggerated for the sake of clarity.

The spongy element 25 is applied against the inner face 26 of rim 16.

Rod 5, back 4, leg 3, shank 8 and the centering tube 21 are pierced with channels or orifices 29 to 33, respectively, for passing therethrough conductors 34 connecting the piezoelectric crystal 20 to the outside.

In addition, in the shoulders connecting the central part 10 to shanks 8 and 10, are formed bearing surfaces 35 and 36 for washers 37 and 38 made from a spongy material. Washers 37 and 38 bear against bearings 14 or 15, through rigid wear and maintenance washers 39 and 40, respectively. The periphery of the spongy washers 37 and 38 is in contact with the inner face 26 of rim 16.

Thus, when the rolling ring 17 is applied to a work piece to be tested (not shown) and when the device is moved so that said ring rolls, the spongy element 25 fills slit 28 with coupling liquid, so that the ultrasonic transducer 20 may be coupled to said work piece through the support window 19, the liquid film filling slit 28, rim 16 and the running strip 17.

As explained above, the formation of bubbles in the coupling liquid and leaks thereof through the bearings 14 and 15 are prevented by the spongy element 25 and washers 37 and 38.

The electric and mechanical contacts between the piezoelectric crystal 20, the window 19 and hub 7 may be provided in any known way, for example by means of a foil and grease (not shown).

Advantageously, hub 7 is made from stainless steel so that the ultrasonic energy losses are low along the axis X—X.

It can thus be seen that, with the invention:

the formation of bubbles in the internal coupling liquid is eliminated and leaks through the bearings mounting the wheel on its hub are avoided;

a probe is obtained which is entirely and readily removable, which facilitates maintenance and repairs;

a compact probe is obtained, since the amount of coupling liquid is small;

a probe is obtained whose acoustic efficiency is high, because of the transmission and/or reception directivity provided by window 19.

What is claimed is:

1. In an ultrasonic testing device of the type comprising a fixed hub with at least one ultrasonic transducer as well as an annular rolling means having an inner face and mounted for rotation on said hub and surrounding said transducer, this latter being mounted on the hub through a support whose external face, opposite said transducer, defines with the inner face of said rolling means a rotational sliding slit, coupling between said support and said rolling means being provided by an ultrasonic coupling liquid present in said slit, there is further provided a spongy resilient element imbibed with said coupling liquid, said element being housed in a recess in said hub and being applied resiliently against the inner face of said rolling means.

2. The device as claimed in claim 1, wherein, on each side of said recess containing the spongy element and coaxially with said hub, are disposed disks of a spongy material carried by said hub and applied by their periphery against the inner face of said rolling means.

3. The device as claimed in claim 2, wherein each of said disks is pressed between a bearing face of the hub and a corresponding ball or plain bearing serving for mounting the rolling means with respect to said hub.

4. The device as claimed in claim 3, wherein a rigid wear and maintenance washer is provided between a spongy disk and the corresponding ball or plain bearing.

5. The device as claimed in claim 1, wherein said transducer is applied against said support by pressure means.

6. The device as claimed in claim 5, wherein said pressure means comprise a nut pressing said transducer through a resilient slug and a centering guide.

7. The device as claimed in claim 5, wherein said hub comprises a passage transversal to the rotational axis of the rolling means and, inside said passage, are arranged said support for the transducer, said transducer, the means for pressing the transducer on its support and said spongy element.

8. The device as claimed in claim 6, wherein the centering guide fits over the periphery of said transducer without damping axial vibrations thereof.

* * * * *